(12) United States Patent
Ruff

(10) Patent No.: US 6,241,747 B1
(45) Date of Patent: *Jun. 5, 2001

(54) BARBED BODILY TISSUE CONNECTOR

(75) Inventor: Gregory L. Ruff, Chapel Hill, NC (US)

(73) Assignee: Quill Medical, Inc., Research Triangle Park, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/324,529

(22) Filed: Oct. 18, 1994

Related U.S. Application Data

(63) Continuation-in-part of application No. 08/055,989, filed on May 3, 1993, now abandoned.

(51) Int. Cl.$^7$ ................................................ A61B 17/08
(52) U.S. Cl. ........................ 606/216; 606/213; 411/456
(58) Field of Search ................................. 606/153, 213, 606/216, 217, 221, 151, 155; 411/456, 457, 904

(56) References Cited

U.S. PATENT DOCUMENTS

| | | |
|---|---|---|
| 709,392 | 9/1902 | Brown . |
| 733,723 | 7/1903 | Lukens . |
| 789,401 | 5/1905 | Acheson . |
| 816,026 | 3/1906 | Meier . |
| 1,142,510 | 6/1915 | Engle . |
| 1,321,011 | 11/1919 | Cottes . |
| 1,728,316 | 9/1929 | Von Wachenfeldt . |
| 1,886,721 * | 11/1932 | O'Brien ............................ 411/456 X |
| 2,201,610 | 5/1940 | Dawson, Jr. . |
| 2,232,142 | 2/1941 | Schumann . |
| 2,254,620 | 9/1941 | Miller . |
| 2,421,193 | 5/1947 | Gardner . |
| 2,472,009 | 5/1949 | Gardner . |
| 2,684,070 | 7/1954 | Kelsey . |
| 2,779,083 | 1/1957 | Eaton . |
| 2,817,339 | 12/1957 | Sullivan . |
| 2,910,067 | 10/1959 | White . |
| 2,988,028 | 6/1961 | Alcamo . |
| 3,068,869 | 12/1962 | Shelden et al. . |
| 3,068,870 | 12/1962 | Levin . |
| 3,123,077 | 3/1964 | Alcamo . |
| 3,166,072 | 1/1965 | Sullivan, Jr. . |
| 3,209,754 | 10/1965 | Brown . |
| 3,214,810 | 11/1965 | Mathison . |
| 3,221,746 | 12/1965 | Noble . |
| 3,234,636 | 2/1966 | Brown . |
| 3,273,562 | 9/1966 | Brown . |
| 3,352,191 * | 11/1967 | Crawford ............................ 411/456 |
| 3,378,010 | 4/1968 | Codling et al. . |
| 3,385,299 | 5/1968 | Le Roy . |
| 3,494,006 * | 2/1970 | Brumlik ............................ 411/456 X |
| 3,525,340 | 8/1970 | Gilbert . |
| 3,586,002 | 6/1971 | Wood . |
| 3,608,095 | 9/1971 | Barry . |

(List continued on next page.)

*Primary Examiner*—Michael Peffley
(74) *Attorney, Agent, or Firm*—Moore & Van Allen, PLLC; Michael G. Johnston

(57) ABSTRACT

A barbed tissue connector is disclosed for use in closing a body wound. The connector includes an elongated body and a pointed end to facilitate insertion of the connector into tissue. A plurality of closely-spaced barbs are disposed on the body from the pointed end of the connector to a predetermined location on the body. The barbs are yieldable toward the body to make it easier to insert the connector in tissue, and the barbs are generally rigid in an opposite direction to hold the connector in the tissue. The body of the connector is substantially rigid and is sufficiently resilient to return to a predetermined position after deflection therefrom. The connector can be manually inserted into the tissue of a patient, or the connector can be inserted by means of an inserting device which is retracted after the connector is in place.

11 Claims, 3 Drawing Sheets

U.S. PATENT DOCUMENTS

| | | |
|---|---|---|
| 3,608,539 | 9/1971 | Miller . |
| 3,683,926 * | 8/1972 | Suzuki .............................. 606/155 X |
| 3,716,058 | 2/1973 | Tanner, Jr. . |
| 3,825,010 | 7/1974 | McDonald . |
| 4,073,298 | 2/1978 | Le Roy . |
| 4,259,959 | 4/1981 | Walker . |
| 4,317,451 | 3/1982 | Cerwin et al. . |
| 4,428,376 | 1/1984 | Mericle . |
| 4,430,998 | 2/1984 | Harvey et al. . |
| 4,434,796 | 3/1984 | Karapetian et al. . |
| 4,454,875 | 6/1984 | Pratt et al. . |
| 4,467,805 | 8/1984 | Fukuda . |
| 4,505,274 | 3/1985 | Speelman . |
| 4,510,934 * | 4/1985 | Batra ................................ 606/148 X |
| 4,531,522 | 7/1985 | Bedi et al. . |
| 4,548,202 * | 10/1985 | Duncan ................................ 606/220 |
| 4,610,251 | 9/1986 | Kumar . |
| 4,635,637 | 1/1987 | Schreiber . |
| 4,637,380 | 1/1987 | Orejola . |
| 4,676,245 | 6/1987 | Fukuda . |
| 4,719,917 | 1/1988 | Barrows et al. . |
| 4,841,960 | 6/1989 | Garner . |
| 4,887,601 | 12/1989 | Richards . |
| 4,976,715 * | 12/1990 | Bays et al. ....................... 606/220 X |
| 4,994,073 | 2/1991 | Green . |
| 4,997,439 | 3/1991 | Chen . |
| 5,002,562 | 3/1991 | Oberlander . |
| 5,007,921 | 4/1991 | Brown . |
| 5,026,390 | 6/1991 | Brown . |
| 5,047,047 | 9/1991 | Yoon . |
| 5,053,047 * | 10/1991 | Yoon ..................................... 606/223 |
| 5,123,913 | 6/1992 | Wilk et al. . |
| 5,192,302 | 3/1993 | Kensey et al. . |
| 5,207,694 | 5/1993 | Broomé . |
| 5,222,976 | 6/1993 | Yoon . |
| 5,246,441 * | 9/1993 | Ross et al. ....................... 606/213 X |
| 5,269,783 | 12/1993 | Sander . |
| 5,320,629 | 6/1994 | Noda et al. . |
| 5,342,376 * | 8/1994 | Ruff ..................................... 606/151 |
| 5,931,855 | 8/1999 | Buncke . |

* cited by examiner

BARBED BODILY TISSUE CONNECTOR

CROSS REFERENCE TO RELATED APPLICATION

This is a continuation-in-part of copending application Ser. No. 08/055,989 filed on May 3, 1993 now abandoned.

BACKGROUND OF THE INVENTION

1. Field of the Invention

This invention relates to a barbed bodily tissue connector, and more particularly, to such a connector which can be used to quickly and effectively close a body wound.

2. Description of the Prior Art

Human wounds are typically repaired with a filament introduced into the tissue by a needle attached to one end. After piercing the opposing faces of the wound, the needle is removed, and the ends of the suture are tied together with at least three overhand knots. Such a technique requires considerable time and expertise on the part of the surgeon. There are also a number of other drawbacks to repairing a wound in this manner. For example, it is very difficult to use sutures to repair wounds where there is insufficient space to properly manipulate the suture, especially those wounds repaired using fiber optic visualization. The suture forms a loop as it is tied, and this loop constricts blood flow to the tissue in its confines, promoting necrosis of the wound margins. Further, if the needle's passage was noncircular, the tissue will be distorted as it is secured by the suture.

Alternatives to conventional sutures are known in the prior art. Staples, as shown, for example, in U.S. Pat. No. 4,994,073, to Green, are often used for approximating the superficial layer of the wound. Staples, however, are generally unsuitable for deeper layers of tissue.

The patent to Alcamo, U.S. Pat. No. 3,123,077, discloses a roughened suture which can be passed through tissue in one direction, but resists movement in the opposite direction. The Alcamo suture, however, still must be sewn, as by a conventional technique, and the trailing end must be secured with knots. Thus, although there is less slippage of the suture in the wound, most of the disadvantages of sutures noted above are also found in the Alcamo suture.

The patent to Tanner, U.S. Pat. No. 3,716,058, discloses a relatively rigid suture with one or more barbs on opposite ends of an arcuate body. One disadvantage of the Tanner suture is that the rigid barbs, which protrude from the suture as it is inserted, will lacerate tissue and prevent retrograde repositioning. Further, since the barbs are only placed at the ends of the suture, the forces applied to the tissue by the barbs will be limited to a relatively small area; this substantially increases the pressure on the blood vessels ensnared by a barb and severely restricts blood flow to the area.

It will be seen from the foregoing that there is a need for a bodily tissue connector which can be placed more expeditiously than sutures, is self-retaining, obviates distortion of the tissue, can close tissue inaccessible to conventional procedures, and which preserves blood flow by broadly distributing the retention force.

SUMMARY OF THE INVENTION

It is an object of the present invention to overcome the aforementioned problems in the prior art and to provide an improved bodily tissue connector.

In accordance with the present invention there is provided a barbed bodily tissue connector comprising: an elongated body having a point formed on one end, the body being formed of a material sufficiently hard for the point to pierce tissue and enable the connector to be inserted in tissue when a substantially axial force is applied to the body; and a plurality of barbs projecting from the body, the barbs being disposed around the periphery of the body along a length of the body which extends from adjacent the one end to a predetermined location on the body, the barbs being configured such that they are yieldable in a direction toward the body and are generally rigid in an opposite direction, and the barbs being sufficiently resilient to return to a predetermined position after deflection therefrom.

In one embodiment of the present invention, the barbed bodily tissue connector includes an elongated body and a plurality of barbs which are disposed in a helical pattern on the body and extend from a pointed end of the connector to a predetermined location on the body. Each barb includes a first side, which forms an obtuse angle with the body, and a second side which forms an acute angle with the body. The body is substantially rigid and sufficiently resilient to return to a predetermined position after deflection therefrom. When the connector is inserted in tissue to repair a wound or reconfigure the tissue, the pointed end pierces tissue and the barbs yield toward the body to facilitate entry of the connector.

When the connector has been placed in a desired position in tissue, the barbs strongly resist movement away from this position. The connector can be inserted by gripping the connector in the hand and pushing the connector into the tissue, by means of a stapling device or the connector can be inserted by means of an inserting device which is withdrawn when the connector is in place.

A principal advantage of the barbed bodily tissue connector of the present invention is that it permits a surgeon to rapidly and securely attach the edges of a wound in bodily tissue or reconfigure the tissue without the necessity for threading and tying numerous individual stitches or for the use of a complicated or elaborate tool to insert the connector. The connector is configured to minimize damage to tissue when inserted and to minimize scarring or tissue necrosis across the wound. The connector is capable of insertion into the faces of a wound, can connect tissue at the bottom of a deep wound, and can connect tissue which is inaccessible to a staple. Finally, the connector of the present invention can be inserted quickly and accurately by a surgeon who only has access to tissue from a small opening or from only one direction, as, for example, during an endoscopic procedure.

Other features and advantages will become apparent upon reference to the following description of the preferred embodiment when read in light of the attached drawings.

DESCRIPTION OF THE PREFERRED EMBODIMENTS

The present invention allows a surgeon to rapidly and securely attach the edges of a wound in bodily and other animal tissue or reconfigure the tissue without the necessity for threading and tying numerous individual stitches or for using a complicated or elaborate tool. As used herein, the term "wound" means an incision, laceration, cut, or other condition where suturing, stapling, or the use of another tissue connecting device might be required.

Figure 1:
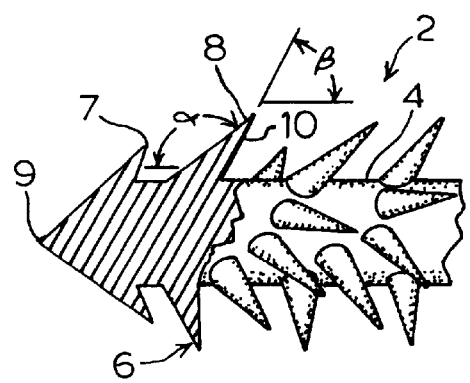
FIG. 1 is a side view of the connector of the present invention, with a section broken away to more clearly show the arrangement of the barbs.
Figure 2:
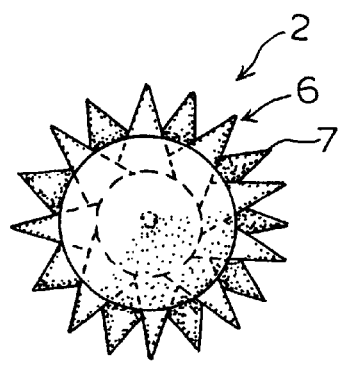
FIG. 2 is an end view of the connector shown in FIG. 1.

With reference to FIGS. 1 and 2, there is shown a barbed bodily tissue connector 2 constructed in accordance with the present invention. Connector 2 includes a body 4 which is generally circular in cross section and a plurality of closely-spaced barbs 6 which extend around the periphery of the body 4. A pointed end 9 is formed on the body 4 to facilitate penetration of the connector 2 into tissue. The body 4 preferably has sufficient dimensional stability to assume a substantially rigid configuration during use and is sufficiently resilient to return to a predetermined shape after deflection therefrom. In some applications, it may be desirable for the body 4 to be flexible and substantially nonresilient so that the shape of an inserted connector will be determined by surrounding tissue.

Barbs 6 serve to hold the connector in tissue and resist retraction of the connector from the tissue. The barbs 6 can be arranged in any suitable pattern, for example, in a helical pattern as shown in FIG. 1. In a helical pattern of barbs 6, it is preferable that the number of barbs occupying one revolution not be an integer, thereby avoiding parallel axial rows of barbs; such an arrangement provides a more uniform distribution of forces on the tissue and lessens the tendency of an inserted connector 2 to cut through tissue. If the number of barbs in one revolution is not an integer, the barbs in successive revolutions will be offset, as shown in FIG. 2, and the amount of offset will determine which barbs are in axial alignment. For example, if the barbs in successive revolutions are offset by ½ barb, the barbs in every second revolution will be in axial alignment, and by extension, if the barbs in each successive revolution are offset by 1/x barb, the barbs in every x revolution will be in axial alignment.

As shown in FIG. 1, each barb 6 includes a first side 8 which forms an obtuse angle alpha with the body 4 and a second side 10 which forms an acute angle beta with the body 4. Each barb 6 tapers to a point 7, and the amount of difference between the angle alpha of side 8 and angle beta of side 10 will control the amount of taper in the barb 6. A barb 6 which tapers from a broad base to a narrow tip can be effective in resisting retraction, yet will yield toward the body 4 during insertion to reduce the effort and tissue damage associated with insertion of the connector 2. The barbs 6 can be generally conical, as shown in FIG. 1, or they can be any other shape which will function in substantially the same manner as the conical barbs.

The configuration of barbs 6 and the surface area of the barbs can vary depending upon the tissue in which the connector 2 is used. The proportions of the barbs 6 can remain relatively constant while the overall length of the barbs and the spacing of the barbs are determined by the tissue being connected. For example, if the connector 2 is intended to be used to connect the edges of a wound in skin or tendon, each barb 6 can be made relatively short to facilitate entry into this rather firm tissue. If the connector 2 is intended for use in fatty tissue, which is relatively soft, the barbs can be made longer and spaced farther apart to increase the holding ability in the soft tissue. If the connector 2 is intended for use in both firm and relatively soft tissue, the barbs 6 along a first length of the connector 2 be made short and the barbs 6 along a second length of the connector 2 can made longer embodiment of the present invetion can be used to connect muscle or tendon to bone.

As shown in FIG. 1, the barbs 6 on connector 2 have a uniform unidirectional configuration, that is, the barbs 6 are uniformly spaced on body 4 and all the sides 8 are oriented in the same direction, facing pointed end 9. Connector 2 can be inserted into tissue with the sides 8 of each barb 6 facing in the direction of motion. Connector 2 will prevent movement of tissue in the direction in which it was inserted. A pair of connectors 2 inserted adjacent to each other and in opposite directions will prevent movement of tissue in either direction across a wound.

Connector 2 can be formed of a material sufficiently hard for point 9 to pierce tissue and enable the connector to be inserted in tissue when a substantially axial force is applied to body 4. Connector 2 is preferably composed of a bioabsorbable compound, such as a polyglycolic acid or polylactic acid polymer or copolymer. The use of a bioabsorbable material eliminates the necessity of removing the connector from the patient, which can be a painful and possibly dangerous process. Connector 2 can be formed, for example, by injection molding The connector 2 can also be hollow or perforated which allows for the retention of therapeutic or other substances therein such as growth hormone, antibiotics and the like.

In one representative example of connector 2 for use in muscular tissue, the body 4 is formed from polyglycolic acid, has a length of 1 to 5 cm, and a diameter of about 1 mm. The diameter of a circle extending around points 7 of barbs 6 will be about 3 mm, and the barbs are spaced apart from each other on body 4 by a distance of 1 mm. Side 8 forms an angle of 135 degrees with the body 4 and side 10 forms an angle of 75 degrees with the body 4.

Figure 3:
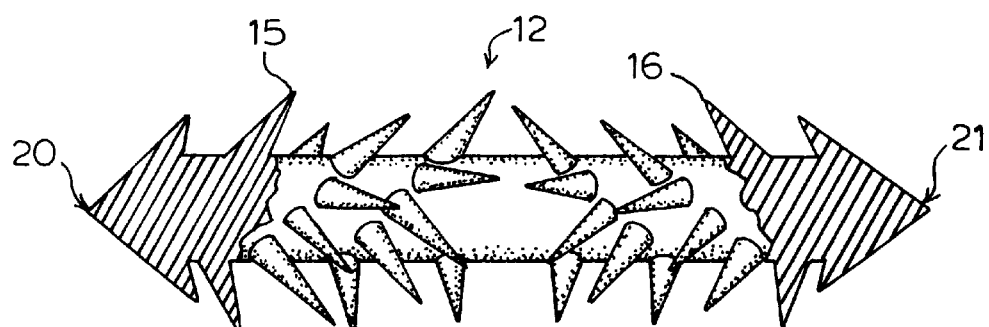
FIG. 3 is a side view of another embodiment of the present invention, with a section of a connector broken away.

In FIG. 3, there is shown a second embodiment of the present invention in which barbs 16 are arranged in a uniform bidirectional configuration on a barbed tissue connector 12. Barbs 16 are constructed in the same manner as barbs 6 on connector 2. A first set of barbs 15 on connector 12 are arranged in a helical pattern and face a pointed end 20, and a second set of barbs 16 on connector 12 are arranged in a helical pattern and face a pointed end 21. Each of the pointed ends 20, 21 should be sufficiently hard and sharp to easily penetrate tissue in which the connector is to be used. Connector 12 is particularly suitable for applications where the edges of a wound are prone to separate. Connector 12 can be used by inserting one of the ends, for example end 20, into a first side of a wound (not shown), spreading the wound slightly to expose the second side of the wound, inserting the end 21 of the connector 12 into the second side of the wound, and then pressing the edges of the wound together. The barbs 15 and 16 on the ends of the connector 12 will grasp the tissue on each side of the wound and prevent the edges of the wound from spreading. The embodiment of the present invention shown in FIG. 3 can also be used as a staple wherein it is inserted hand or by means of a stapling device into adjacent tissue portions.

Figure 4:
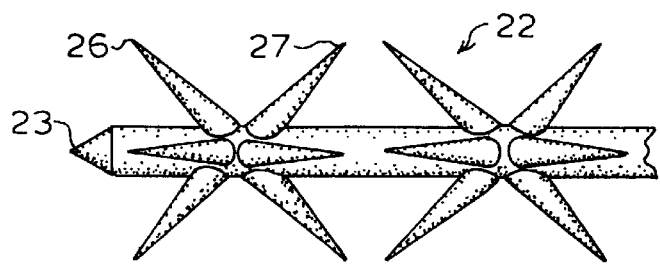
FIG. 4 is a side view of another embodiment of the present invention.

With reference to FIG. 4, there is shown another embodiment of the present invention in which a barbed bodily tissue connector 22 has a nonuniform bidirectional configuration. Connector 22 comprises a pointed end 23 and one or more barbs 26 facing a first direction which alternate with one or more barbs 27 facing a second direction. At each axial location, there can be a number, e.g. 4–9, of circumferentially-spaced barbs 26 or 27. To insert connector 22 into tissue, the surgeon would use an inserting device 80 as described below. The arrangement of barbs 26, 27 on connector 22 would prevent any localized movement of tissue relative to the connector in an axial direction.

Figure 5:
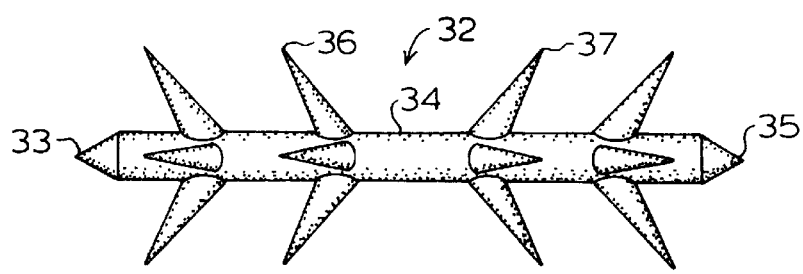
FIG. 5 is a side view of another embodiment of the present invention.

With reference to FIG. 5, there is shown another embodiment of the present invention in which a barbed tissue connector 32 has a uniform bidirectional configuration. Connector 32 comprises a body 34 having pointed ends 33 and 35. A plurality of axially-spaced barbs 36 adjacent pointed end 33 face toward end 35, and a plurality of axially-spaced barbs 37 adjacent pointed end 35 face toward end 33. Barbs 36 and 37 can be circumferentially-spaced around body 34 at each axial location, or the barbs 36 and 37 can be of the same construction and arranged in the same pattern as barbs 6 on connector 2. To insert a connector 32, the surgeon would use an inserting device 80 as described below. If the body 34 of the connector 32 is sufficiently rigid, the connector 32 would prevent tissue retained by the barbs 36 from moving toward end 35 and tissue retained by barbs 37 from moving toward end 33. It will be apparent that only one end of connector 32 needs to be pointed; two pointed ends are preferable, however, so that the surgeon does not have to take the time to insure that connector 32 is oriented in the inserting device 80 with a pointed end protruding from the inserting device.

Figure 6:
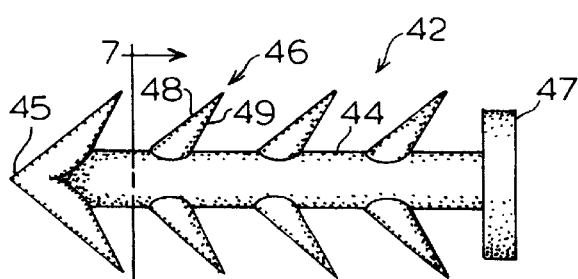
FIG. 6 is a side view of another embodiment of the present invention.
Figure 7:
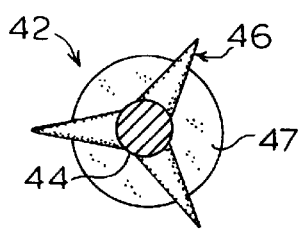
FIG. 7 is a sectional view taken along the line 7—7 in FIG. 6.

With reference to FIGS. 6 and 7, there is shown another embodiment of the present invention in which a barbed bodily tissue connector 42 comprises a body 44 having a pointed end 45 for penetration into tissue. A head 47 is formed on an opposite end of body 44. A plurality of circumferentially-spaced barbs 46 are formed on body 44 at each of a number of axial locations. As shown in FIG. 7, three barbs 46 are formed at each axial location; however, more or less than three barbs 46 could be used for certain applications. Barbs 46 include a first side 48 formed at an obtuse angle to the body 44 and a second side 49 which projects from body 44 at an acute angle. The connector 42 can be forced into tissue by applying a force to the head 47.

The connector 42 can be applied by hand, or it can be inserted using an inserting device 80 as described below.

The connector 42 can be formed entirely of a bioabsorbable material, or the head 47 and the body 44 can be composed of different materials. For example, the body 44 can be composed of a bioabsorbable material, and the head 47 can be composed of metal for superior strength and to facilitate insertion of the connector 42. Head 47 can be made flat, as shown in FIG. 6, or the head can be formed by a single ring of barbs (not shown) facing in a direction opposite to that of the barbs 46.

In use, a series of connectors 42 can be inserted into tissue, such as along the edges and in the field of a skin graft. After an adequate amount of time has passed for the wound to heal, the tissue beneath each head 47 could be depressed slightly to permit the head 47 to be cut from the body 44. The tissue would then rise up over the cut end of the body. Such a process would reduce scarring which could result from a long-term projection of the body 44 through tissue and would eliminate the necessity to remove connectors 42 from the patient.

Figure 8:
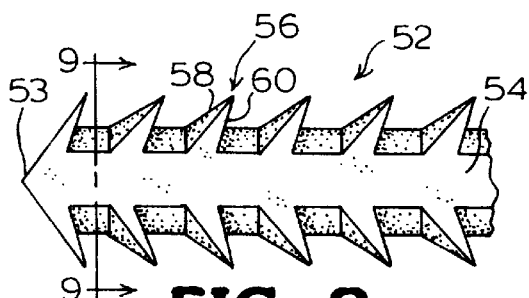
FIG. 8 is a side view of another embodiment of the present invention.
Figure 9:
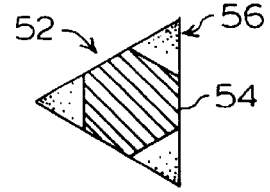
FIG. 9 is a sectional view taken along the line 9—9 in FIG. 8.

With reference to FIGS. 8 and 9, there is shown another embodiment of the present invention in which a barbed bodily tissue connector 52 has a uniform unidirectional configuration. Connector 52 comprises a body 54 having a non-circular cross-sectional shape. Body 54 includes a plurality of barbs 56 which are generally triangular in cross section and are equally spaced around the periphery of the body at a series of axial locations. Each of the barbs 56 includes a first side 58 disposed at an obtuse angle to body 54 and a second side 60 disposed at an acute angle to the body. Body 54 includes a pointed end 53 to facilitate entry in tissue. Use of a non-circular cross-sectional shape increases the surface area of the connector 52 and facilitates the formation of the multiple barbs on the connector. For example, barbs 56 can be formed on a piece of stock having a triangular cross section by removing material at successive axial locations from the three edges of the stock. It will be apparent that a similar process could be used to form barbs on stock of a different cross section (not shown), for example, a rectangular or hexagonal cross section.

Figure 10:
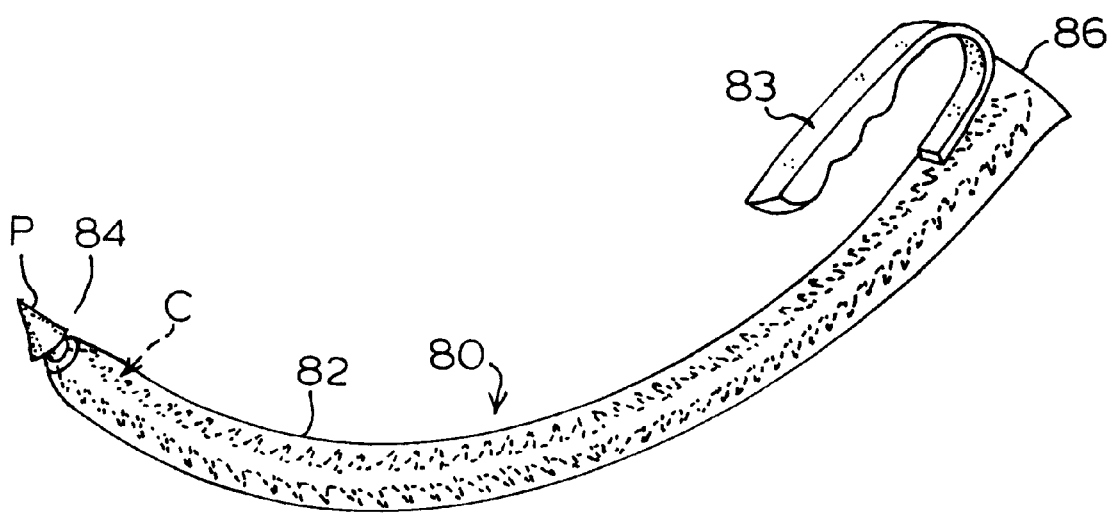
FIG. 10 is a perspective view of an inserting device for use with a barbed bodily tissue connector of the present invention.
Figure 11:
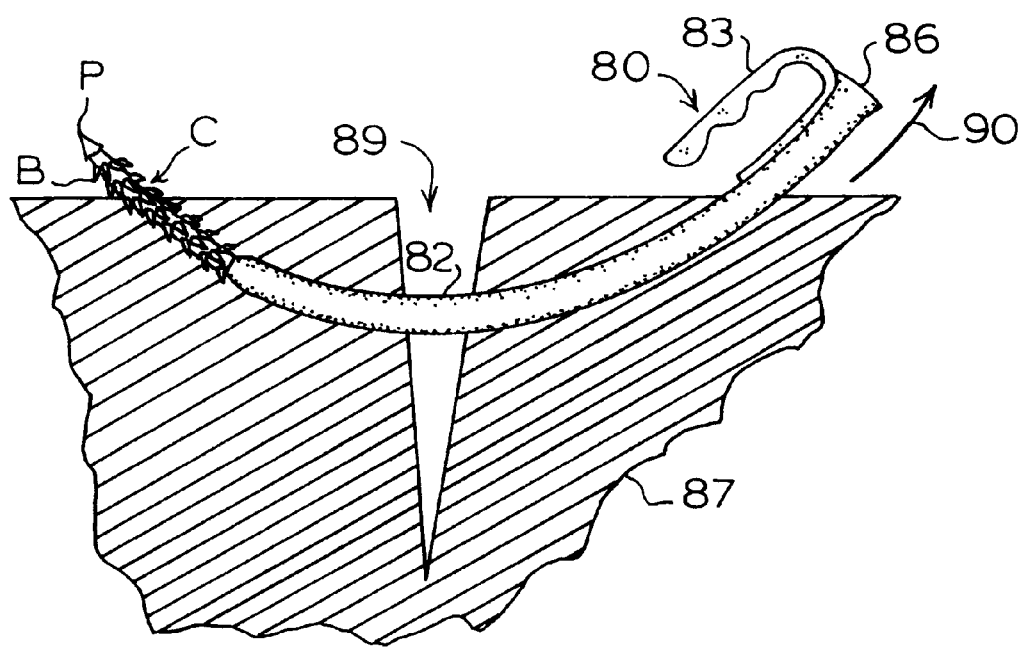
FIG. 11 is a view showing the inserting device and connector in a wound.

In the use of the disclosed connectors, such as connectors 2 and 42, the surgeon can grip the connector in one hand and push the connector into the tissue. As an alternative to directly inserting the connectors into the tissue, the surgeon can use an inserting device 80 as shown in FIGS. 10 and 11 and more fully described in U.S. Pat. No. 5,342,376. The inserting device 80 comprises a circular tubular body 82. The tubular body 82 can be generally arcuate in an axial direction, and the body 82 is sufficiently long to contain-at least a portion of a barbed bodily tissue connector C. Device 80 has an inwardly tapered leading end 84 and an outwardly tapered, or flared, trailing end 86. A handle 83 is provided on body 82 adjacent trailing end 86 to enable the surgeon to manipulate the inserting device 80.

In order to facilitate entry of the connector C and the device 80 into tissue, a connector C is positioned in tubular body 82 with a pointed end P of the connector C extending from leading end 84. In a preferred embodiment, the interior diameter of the body 82 is made slightly smaller than the outside diameter of the connector C so that the barbs B of a connector C in the body 82 will press against the body 82; as a result, the connector C will be retained in the body 82 during insertion in tissue with the point P properly positioned outside of the body 82. The connector can also be positioned in body 82 with a barb B outside of body 82 to insure that the connector C will not be pushed back in the body 82 during insertion. In one application of device 80, the surgeon inserts the body 82 having connector C therein into the patient's tissue 87 until the connector C reaches a desired position, for example, the position shown in FIG. 11. Device 80 is then withdrawn in the direction of arrow 90, and a barb, or barbs, B on the connector C penetrates and catches the tissue 87 to hold the connector C in the inserted position.

Use of the inserting device 80 is particularly recommended when the connector C includes multiple barbs facing more than one direction, such as connectors 22 and 32, or when the connector is too flexible for insertion without additional support.

The connector can also be sewn into tissue, as by a conventional technique. However, with the connector of the present invetion, ti is not necessary to secure the trailing end with knots as with the Alcamo suture described above.

While the present invention has been described with respect to certain preferred embodiments thereof, it is to be understood that numerous variations in the details of construction, the arrangement and combination of parts, and the type of materials used may be made without departing from the spirit and scope of the invention.

What is claimed is:

1. A barbed bodily tissue connector for connecting bodily tissue to permit healing or reconfiguration in vivo, comprising:

an elongated body having a first end and a second end, an end adapted to penetrate the tissue for facilitating insertion of the connector into the tissue, the body being formed of a material sufficiently hard for the penetrating end to pierce the tissue and enable the connector to be inserted into the tissue when a substantially axial force is applied to the body; and a plurality of barbs projecting from the periphery of the body, a portion of the barbs facing the first end and the remaining barbs facing the second end, the barbs being generally rigid in an opposite direction from which the barbs are facing for resisting movement of the connector in an axial direction relative to the body, and the connector insertable into adjacent tissue portions so that a barb facing the first end of the connector penetrates a first adjacent tissue portion and a barb facing the second end of the connector penetrates a second adjacent tissue portion so as to inhibit relative movement of the connector, the barbs defining means for engaging the tissue such that the retention force on the tissue in the engaging area is broadly and uniformly distributed for preventing distortion of the tissue and preserving blood flow in the engaging area minimizing scarring and necrosis of the tissue.

2. A barbed bodily tissue connector as recited in claim 1, wherein the barbs are formed in a helical pattern on the body.

3. A barbed bodily tissue connector as recited in claim 1, wherein successive revolutions of the barbs are offset in a circumferential direction by 1/x barb whereby the barbs on the body are in axial alignment every x revolutions.

4. The barbed bodily tissue connector as recited in claim 1, wherein the body has sufficient dimensional stability to assume a substantially rigid configuration during use thereof.

5. The barbed bodily tissue connector as recited in claim 1, wherein the body is sufficiently resilient to return to a predetermined shape after deflection therefrom.

6. The barbed bodily tissue connector as recited in claim 1, wherein the body is flexible and substantially nonresilient whereby the shape of an inserted connector will be determined by the surrounding tissue.

7. The barbed bodily tissue connector as recited in claim 1, wherein certain adjacent barbs face toward each other.

8. The barbed bodily tissue connector as recited in claim 1, wherein the body has a head formed thereon at a second end.

9. The barbed bodily tissue connector as recited in claim 1, wherein the body is formed of a bioabsorbable material.

10. The barbed bodily tissue connector as recited in claim 1, wherein the barbs projecting from the periphery of the body along a length of the body extending from adjacent the first end to a first axial location on the body face the first end, and the barbs projecting from the periphery of the body along a length of the body extending from adjacent the second end to a second axial location on the body which is less than the distance from the second end to the first axial location on the body face the second end.

11. The barbed bodily tissue connector as recited in claim 1, wherein the barbs projecting form the periphery of the body along a length of the body extending from adjacent the first end to a first axial location on the body face the second end, and the barbs projecting from the periphery of the body along a length of the body extending from adjacent the second end to a second axial location on the body which is less than the distance from the second end to the first axial location on the body face the first end.

* * * * *